US009463460B2

(12) United States Patent
Kumaran et al.

(10) Patent No.: US 9,463,460 B2
(45) Date of Patent: Oct. 11, 2016

(54) MICROFLUIDIC DEVICE

(71) Applicant: INDIAN INSTITUTE OF SCIENCE, Bangalore (IN)

(72) Inventors: V Kumaran, Bangalore (IN); Mohan K. S. Verma, Bangalore (IN)

(73) Assignee: INDIAN INSTITUTE OF SCIENCE, Bangalore (IN)

(*) Notice: Subject to any disclaimer, the term of this patent is extended or adjusted under 35 U.S.C. 154(b) by 0 days.

(21) Appl. No.: 14/312,754

(22) Filed: Jun. 24, 2014

(65) Prior Publication Data

US 2015/0367344 A1 Dec. 24, 2015

(30) Foreign Application Priority Data

Jun. 23, 2014 (IN) .......................... 3020/CHE/2014

(51) Int. Cl.
*G01N 33/00* (2006.01)
*B01L 3/00* (2006.01)

(52) U.S. Cl.
CPC .... *B01L 3/502746* (2013.01); *B01L 3/502761* (2013.01); *B01L 3/502776* (2013.01); *B01L 2200/0652* (2013.01); *B01L 2300/0838* (2013.01); *B01L 2300/0867* (2013.01); *B01L 2300/0887* (2013.01); *B01L 2300/123* (2013.01); *B01L 2400/0655* (2013.01); *B01L 2400/084* (2013.01)

(58) Field of Classification Search
CPC .................. B01L 3/502776; B01L 2200/0652
See application file for complete search history.

(56) References Cited

PUBLICATIONS

M. K. S. et al., A multifold reduction in the transition Reynolds number, and ultra-fast mixing, in a micro-channel due to a dynamical instability induced by a soft wall, Journal of Fluid Mechanics / vol. 727 / Jul. 2013, pp. 407-455.

*Primary Examiner* — Sam P Siefke
(74) *Attorney, Agent, or Firm* — Sughrue Mion, PLLC

(57) ABSTRACT

A microfluidic device of the present invention is connected to at least an inlet to permit at least a stream of fluid with a desired fluid flow rate and a stable laminar flow. A body with at least a non-deformable portion and a deformable portion is connected to the inlet. At least a microconduit of substantially reduced length and cross-section, integrally formed in said non-deformable and deformable portions, and connected to the inlet. The stable laminar flow of fluid transiting through the microconduit is disrupted, resulting in a turbulent flow of the fluid, with a vibration of the deformable portion, when the fluid flow rate crosses a threshold value. The turbulent flow of the fluid undergoes an enhanced mixing, in a reduced period of time. At least an outlet is connected to microconduit to collect the mixed fluid. A network of microfluidic devices are arranged to perform mixing of fluids.

18 Claims, 11 Drawing Sheets

(a)

(b)

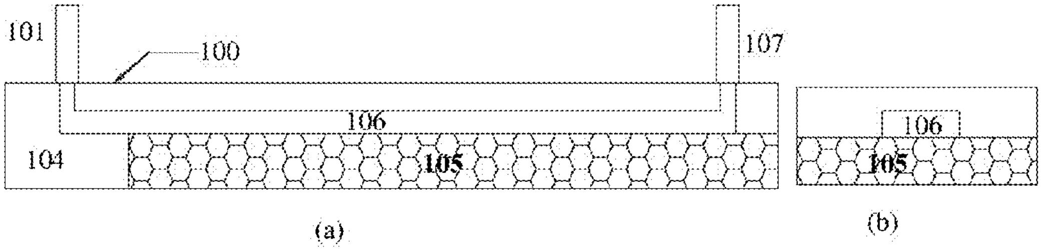
FIG.2 (a) & (b)
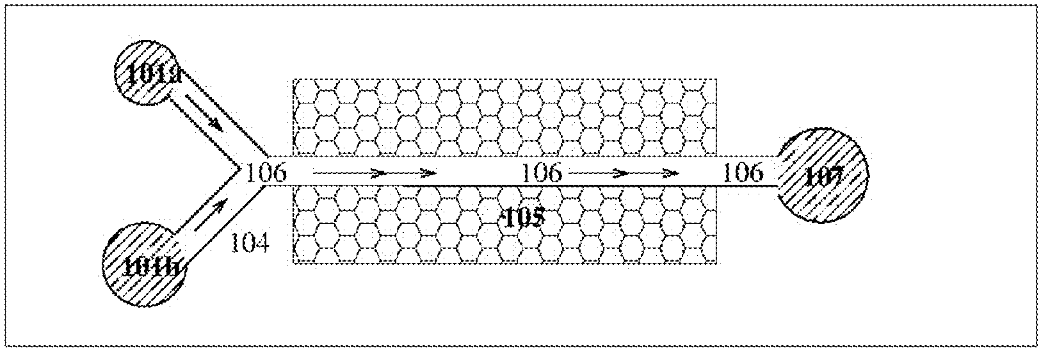
FIG.3

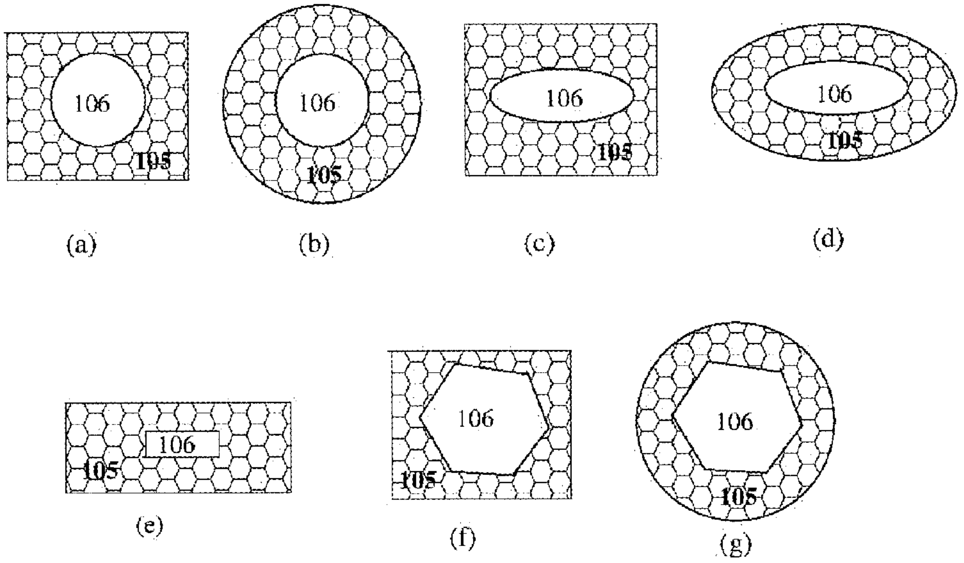
FIG. 4 (a)-(g)
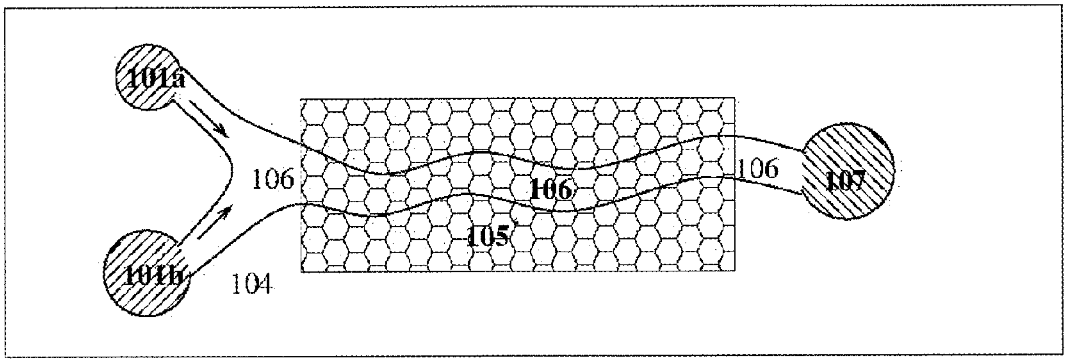
FIG.5

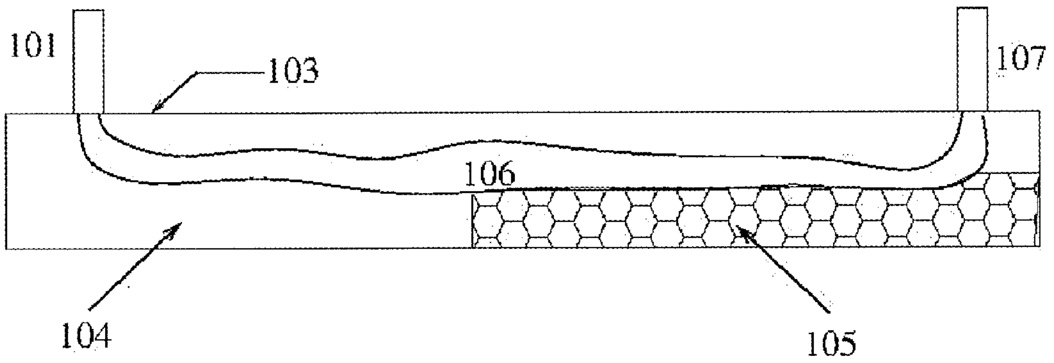
FIG.8
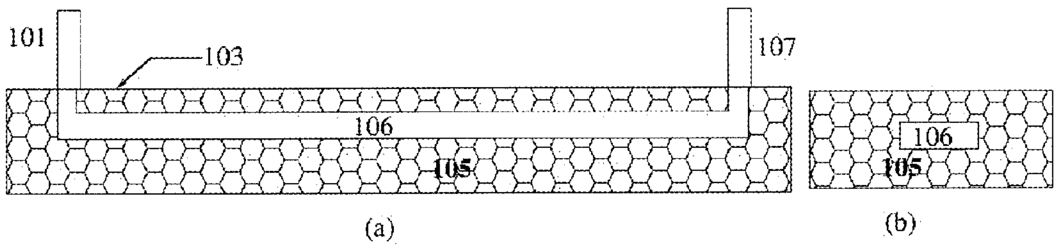
FIG. 9 (a)-(b)

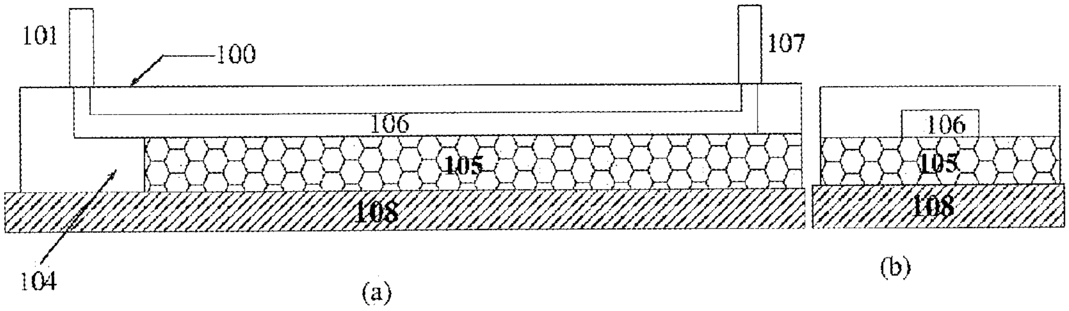
FIG. 10 (a)-(b)
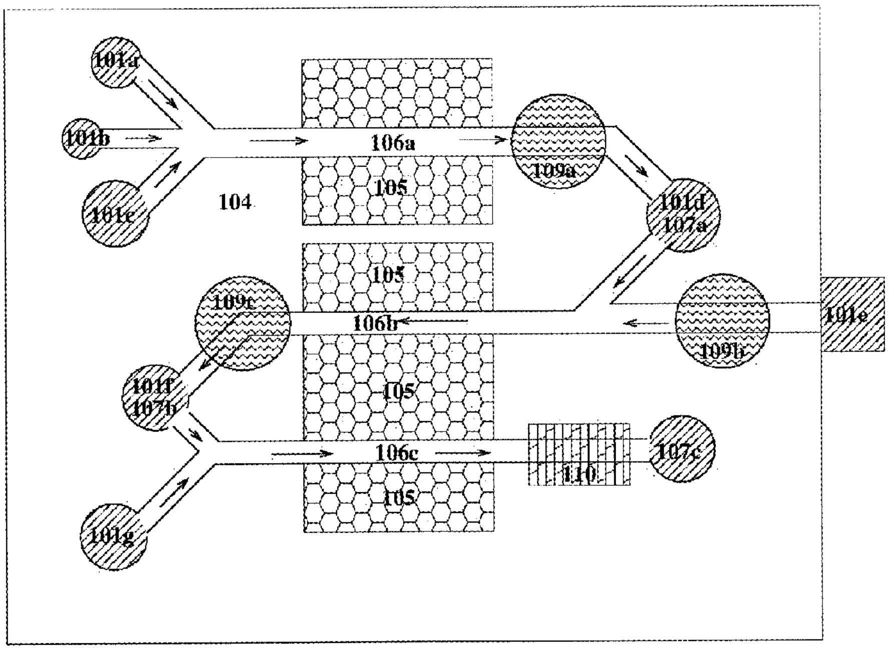
FIG.11

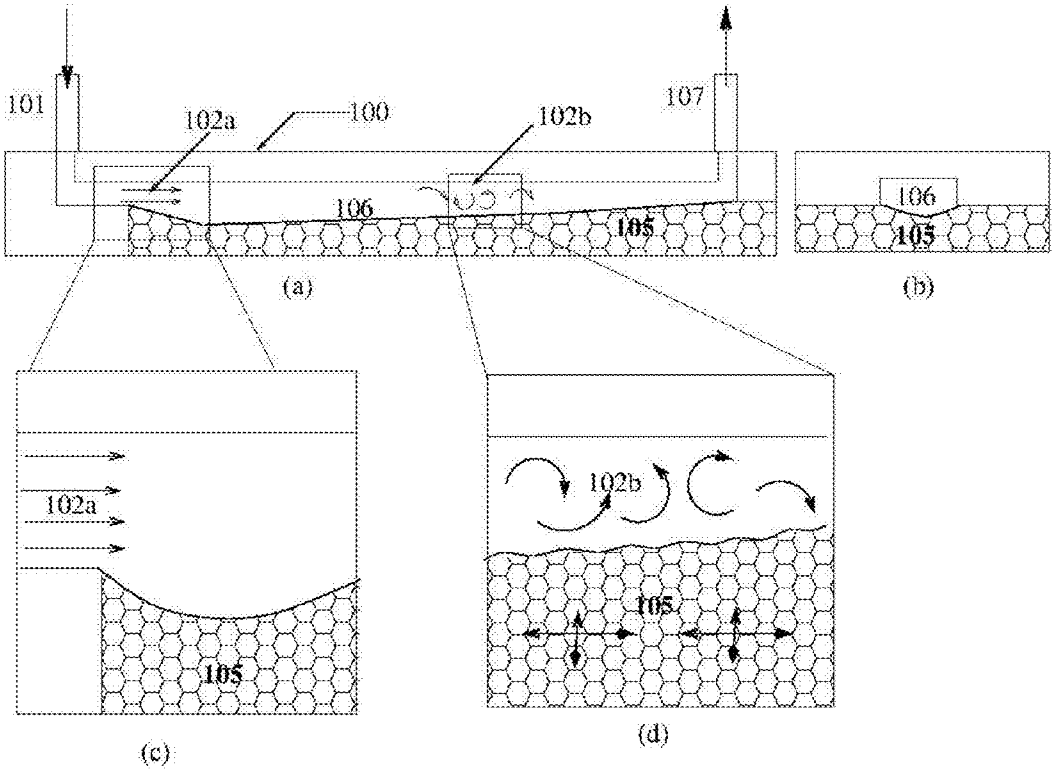
FIG.12(a-d)
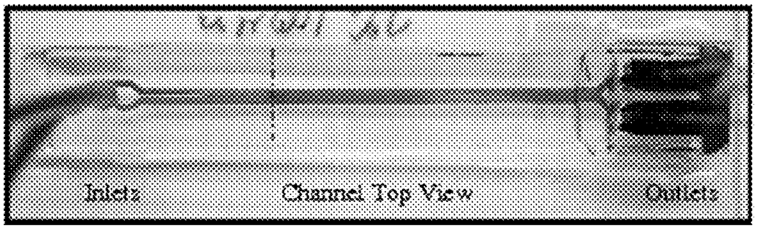
FIG.13

MICROFLUIDIC DEVICE

TECHNICAL FIELD

The present invention relates generally to microfluidic devices. More particularly, the present invention provides a microfluidic device having microfluidic conduit(s) to render enhanced mixing of fluid(s), in a reduced period of time, by inducing turbulence in laminar flow of the fluid(s).

BACKGROUND OF THE INVENTION

Microfluidic technologies have the potential to transform industries where high-value chemicals are processed in small quantities, such as health care, medical diagnostics, fine chemicals, etc. Some diagnostic devices, such as glucose meters and immunoassays are in use. Successful devices typically involve capillary action for fluid transport, and they do not incorporate fluid pumping or mixing within the device.

There are technological challenges to down-scaling processes that involve mixing, heating/cooling, pumping, reacting and metering of fluids, due to which there are no commercially available products that carry out these complex operations.

At small scales, fluid flow is in the laminar regime, and mixing takes place by molecular diffusion. This is in contrast to large scale industrial processes, where the flow is usually in the turbulent regime; turbulent mixing is faster, by orders of magnitude, in comparison to molecular diffusion. To provide a perspective, the diffusion coefficient of small molecules in liquids such as water is of the order of $10^{-9}$ $m^2/s$, and that of larger molecules such as proteins could be as low as $10^{-13}$ $m^2/s$. Based on simple dimensional analysis, the time required for diffusion across a channel of width 1 mm could be as long as 1000 s for small molecules, and as large as $10^7$ s for larger molecules.

Due to the slow mixing, it is necessary for fluids to remain in contact for long periods of time. A blood cell counter requires a path length of many tens of centimeters so that the flow contact time is sufficient for the blood and cell lysing agent to mix completely.

In a micro fluidic device as the path length increases, the pressure drop for driving the flow also increases (proportional to the length). The pressure drop across a micro-channel of length 1 m, width 1 mm and height 100 μm can be as large as 4-5 atm even for a very small flow rate of 1 ml/min when the flow is laminar. Such large pressure drops require pumps and compressors to drive the flow, and increase the complexity and cost of equipment involved. Such large pressure drops require a high mechanical strength of the device itself, since high pressures in systems of small dimensions could lead to mechanical failure. The large path length also increases the volume of fluids and expensive reagents that are required.

There is also the difficulty of setting up fluid interconnects between the device and the surrounding fluid inputs or outputs which are strong enough to withstand the high pressures without leakage.

In view of the foregoing reasons microfluidic devices for pumping, mixing, heating/cooling, reacting, metering and other handling of fluids typically involve large path lengths (of the order of tens of centimeters), due to the slow mixing. In microfluidic applications, where the Reynolds number is low because the channel/pipe diameter is small, the flow is usually in the laminar regime. Here, the Reynolds number is ($\rho V L/\eta$), where $\rho$ and $\eta$ are the fluid density and viscosity, L is the characteristic length (tube diameter or channel height) and V is the characteristic velocity. In a laminar flow with smooth streamlines, mixing occurs only by molecular diffusion, which is much slower than turbulent diffusion. Therefore, one encounters the engineering limitation that the rates of mass and heat transfer are much lower than that in a turbulent flow. This results in the requirement for long fluid paths in order to provide adequate residence time for mixing, and the consequent increase in the pressure requirements for pumping the fluid at low velocities. The devices are typically connected to external inlets and outlets and driven by external pumps and compressors. Moreover, the large pressure differences often result in mechanical failure of the equipment due to the inability of the tubes and channels to withstand the large forces.

Complex microfluidic circuits with large numbers of tubes, valves and actuators, which resemble electronic integrated circuits, have been fabricated. The fluid flow in these typically is driven by positive displacement syringe pumps or by pressure sources and the valves are also opened and closed by pressure sources. The requirement of external connections makes the device more complex and inflexible in its operation. Even though the microfluidic device itself is very small in size (one square centimeter or less), there are a large number of large external devices connected to it, such as syringe pumps, piston pumps, compressors, electrical and magnetic actuators, etc.

The important technological bottleneck to developing smaller and less complex networks is the slow mixing in these devices. Several proposals for enhancing mixing in micro-channels and micro-tubes have been proposed. However, these strategies have the undermentioned limitations.

Passive mixing due to tortuous channels or due to roughness at the boundaries. These include channels with repeated bends to curve the streamlines, wall grooves to introduce secondary flows, hydrodynamic focusing where substantially different flow rates come into contact, split-and-recombine strategies (splitting the inlet into a large number of small streams using channel bifurcations and then recombining them by an inverse bifurcation) either in parallel or in series. These require expensive fabrication techniques, where micron and sub-micron features have to be etched in silicon. This increases the path-length of the flow and consequently the pressure drop and the power required. This also increases cost due to complexity of fabricating tortuous channels or sub-micron structures.

Mixing by using electric or magnetic fields in to exert forces on ions within fluids containing ionic entities, due to the electrodynamic or magnetic forces exerted on the ions or suspended magnetic particles. This approach is applicable only for fluids which have suspended ions or magnetic particles, and it involves separations in case the particles are added specifically for driving the flow. The pumping or mixing efficiency in these systems is sensitive to the concentrations of the ions or magnetic particles. The system also becomes more complicated and expensive due to the requirement of external electrical and magnetic circuits.

Active mixing, using displacement of elements within the tube or channel by external means in order to generate a more complicated flow profile and thereby enhance mixing. Active strategies include pressure pulsing, electro-kinetic disturbances induced due to fluctuating electric fields, actuation by acoustic waves, and micron sized stirring devices. This involves moving parts of microscopic scale in order to generate displacements and produce mixing. This increases the complexity and cost of fabrication significantly, and the pressure drop required to drive flow is also significantly higher.

Droplet microfluidics, where the fluid is processed within a droplet, which is in turn suspended within an external immiscible fluid. The mixing in droplet microfluidics is usually generated by flow within the droplet due to the fluid motion around the droplet. This concept could be useful for pure fluids which do not contain suspended particles such as blood cells, but it is difficult to use for fluids with suspended particles, since the droplet size could be similar to the size of the suspended particles. There are other disadvantages as well. Complex channel shapes are usually required to enhance mixing and these increase the pressure drop, power requirement, and cost. The inlet manifolds and the controls are also more complicated since two fluids have to be injected in specified sequence at pre-determined rates. Droplets can be combined and separated and moved in pre-specified paths, but these require intricate controls which increase complexity and cost of the device. Further, separation of the droplets after processing is necessary to recover the products.

The technology barrier due to slow mixing has been well recognized for some time now. In fluid mechanics, rapid mixing is often achieved by disrupting the laminar flow and making the flow turbulent. Turbulent flows have mixing rates that are orders of magnitude higher than those of laminar flows. The transition to turbulence takes place when the Reynolds number exceeds a threshold value, which is about 1000 for the flow in a channel and about 2100 for the flow in a tube. Flows are usually turbulent in large scale applications, where the flow exhibits violent and unsteady motion, and mixing is rapid due to turbulent 'eddies' (parcels of fluid in correlated motion). In microfluidic applications, flows are usually laminar, because the dimensions are small and the Reynolds number is lower than the threshold value.

The laminar-turbulent transition in tube flows continues to be an active area of research over a hundred years after it was discovered. It is fair to say that the exact transition mechanism is still not clear, and this transition cannot be captured by standard methods of stability analysis.

In the flow through flexible tubes, there theoretical studies have shown that there could be instability due to the interaction between the fluid and wall material. This instability could occur at a Reynolds number lower than 2100, provided the wall material is sufficiently soft. The instability mechanism, which involves wall oscillations due to the coupling between the fluid and wall dynamics, is qualitatively different from the transition mechanism in rigid tubes. The transition Reynolds number is a function of the dimensionless $\Sigma=(\rho GR^2/\eta^2)$, the ratio of the elastic forces in the wall material and the viscous forces in the fluid. Here, G is the shear modulus of the wall material, R is the tube radius, and $\rho$ and $\eta$ are the fluid density and viscosity.

It is also known that there could be instability even at Reynolds number less than 1, provided the fluid has very high viscosity (about 1000 times the viscosity of water) and the wall of the channel/tube is made sufficiently soft. A modest enhancement in the mixing rates of about 25% is also known, due to the instability at low Reynolds number. However, it is infeasible to use such low Reynolds number flows of very viscous fluids for microfluidic applications. Large pressure gradients required to drive very viscous fluids through conduits of small dimension would break apart conduit and rupture connections.

It was previously considered to be infeasible to use this mechanism for microfluidic applications where the Reynolds number with fluids having low viscosity from 1 to 10 times the viscosity of water at standard conditions, because the instability can be triggered at a Reynolds number less than the transition Reynolds number of 1000 in a channel only if the wall elasticity is less than 1 kPa, which is difficult to realize in practice. Our experiments show that the transition Reynolds number can be reduced below 1200 even with soft materials of shear modulus 100 kPa, which are achievable in practice. Thus, it is possible to induce instability of the laminar flow and enhance mixing just by making the tube walls soft in microfluidic applications. This opens up the opportunity for tailoring sections in microfluidic applications to have soft walls, which spontaneously oscillate in the presence of fluid flow in order to induce mixing.

The instability in the flow through soft tubes of diameter 1.2 and 0.8 mm and of length between 14.5 and 20 cm, were studied experimentally by M. K. S. Verma and V. Kumaran and the work was published in the *J. Fluid Mech.,* 705, 322-347, 2012, under the title "*A dynamical instability due to fluid-wall coupling lowers the transition Reynolds number in the flow through a flexible tube*". It was observed in this document that the transition Reynolds number could be reduced below the value of 2100 for a rigid tube, and the lowest transition Reynolds number of about 500 was achieved for the softest tubes used in the experiments. Though the objective of inducing a disruption of the laminar flow was achieved, the device was not found suitable for rapid mixing of fluids for many reasons such as the minimum dimension that could be achieved in the disclosed device was 0.8 mm, whereas for microfluidic applications, a minimum cross-section dimension of less than 500 μm, preferable 200 μm, is necessary. Moreover, fabrication of microconduits of length 15-20 cm was also challenging task for use in microfluidic applications, since the dimensions of the known devices are in the order of 3-5 cm. More significantly, the disclosed device does not disclose a complex network of microconduits that can be used in micro fluidic applications.

In this disclosed device, it was observed that even though there was instability of the fluid flow after transition from the laminar flow of the fluid, the velocity fluctuations in the flow were not large enough that could result in turbulent flows, since the turbulent velocity fluctuations were typically measured at not more than 10% of the mean flow velocity, which were much smaller than those in turbulent flows, where typically the fluctuations are at least 50% or more of the mean flow velocity. Consequently, mixing efficiency of the fluids in the device was poor. The mixing of fluids was examined by injecting a dye-stream at the center of the tube, and observing the dye-stream as it progressed through the tube. In the laminar flow, the dye-stream followed a straight line path with no cross-stream disturbance. After transition, the dye-stream was disrupted, but even at the end of a tube of length 5 cm, as shown in FIG. 1, it was observed that there is an uneven distribution of dye across the tube, with most of the dye concentrated in blobs at the center. In order to measure the quality of mixing, the mixing index can be defined as a measure of the uniformity of concentration at the end of the device when two streams, one containing dye or solute and the other with no dye or solute, are introduced at the inlet. In this experiment the average concentration across the entire cross section of the device is subtracted from the local concentration to obtain the concentration fluctuations. The root mean square of the concentration fluctuations is divided by the average concentration to obtain the segregation index $S_I$. The mixing index is defined as $M_I=(1-2\ S_I)$. The mixing index is 1.0 for perfectly mixed streams, and is 0.0 when there is no mixing between the two streams. In dye stream experiments on the flow through tubes in prior work, the mixing index does not exceed 0.4 even after transition, indicating very imperfect mixing.

Therefore, due to the combination of poor mixing and small cross-stream velocity fluctuations, it was considered infeasible to use the devices of this nature to generate rapid mixing in still smaller devices, since for microconduits of the length 3-5 cm and with the height of about 200 μm and 3-5 cm in length, the residence time of the fluid in the microconduit becomes smaller, by a factor of 4 to 6 in comparison to a tube of length 20 cm. Due to this, the small magnitude of the velocity fluctuations results in poor mixing of fluids in such devices.

It is also desirable to develop devices that can carry out multiple sample preparation and/or physical/chemical transformation steps such as mixing and reactions, heating/cooling, metering, and pre-determined time delays for the completion of reactions or physical transformation of fluids such as blood which could contain suspended particles. These devices are required to have pre-loaded reactants/reagents/sample conditioners of precise and tunable volumes, which can be mixed together for sample preparation in the case of diagnostics or for point-of-delivery adjustment of reactant volumes in the case of chemical synthesis. It is also desirable to carry out multiple operations in series or parallel, and the system should be fluidically insulated from the surroundings, apart from sample loading or product collection for diagnostics or therapeutics either externally or integrated with the device, in order to maintain sterility and avoid contamination.

Complex microfluidic circuits with large numbers of tubes, valves and actuators, which resemble electronic integrated circuits, have been fabricated. The flow in these typically is driven by positive displacement syringe pumps or by pressure sources and the valves are also opened and closed by pressure sources. The requirement of external connections makes the device more complex and inflexible in its operation. Even though the microfluidic device itself is very small in size (one square centimeter or less), there are a large number of large external devices connected to it, such as syringe pumps, piston pumps, compressors, electrical and magnetic actuators, etc. Even though these devices are commonly called lab-on-a-chip' devices, they are actually 'chip-in-a-lab' devices which require large laboratory equipment to drive the flows. The technological bottleneck to developing smaller and less complex networks is the slow mixing in these devices.

Objects of the Present Invention

The primary object of the present invention is to provide a microfluidic device with at least a microconduit, having a non-deformable section and a deformable section, to trigger instability in the laminar fluid flow, while fluid is transiting through the microconduit.

An object of the present invention is to provide a microfluidic device with at least a microconduit, which can significantly enhance mixing of fluid, in the deformable section of the device, due to disruption of the laminar fluid conditions.

Another object of the present invention is to provide a microfluidic device to render an enhancing mixing of fluids under turbulent conditions, in a reduced period of time.

Yet another object of the present invention is to provide a microfluidic device with at least a microconduit having a deformable section, the spontaneous oscillation of which accompanies the disruption of the laminar flow and the enhanced mixing.

Still another object of the present invention is to provide a microfluidic device with at least a microconduit having a deformable section, where the instability in the fluid, which causes the disruption of the laminar flow of the fluid, is triggered only when the flow rate of the fluid (Reynolds Number) exceeds a critical or desired value.

It is also an object of the present invention to provide a microfluidic device with at least a microconduit with a substantially smaller dimension in the range of about 20-500 μm and with a reduced length.

Yet another object of the present invention is to provide a microfluidic device with at least a microconduit, which is made of soft material having a shear modulus below 100 kPa and the transition Reynolds Number (Re) less than 2100.

Further object of the present invention is to provide a microfluidic device with a network of microconduits, having a combination of non-deformable and deformable portions.

SUMMARY OF THE PRESENT INVENTION

The present invention provides a microfluidic device connected to at least an inlet to permit at least a stream of fluid with a desired fluid flow rate and a stable laminar flow. A body with at least a non-deformable portion and a deformable portion is connected to the inlet. At least a microconduit of substantially reduced length and cross-section, integrally formed in said non-deformable and deformable portions, and connected to the inlet. The stable laminar flow of fluid transiting through the microconduit is disrupted, resulting in a turbulent flow of the fluid, with a vibration of the deformable portion, when the fluid flow rate crosses a threshold value. The turbulent flow of the fluid undergoes an enhanced mixing, in a reduced period of time. At least an outlet is connected to microconduit to collect the mixed fluid.

DEFINITIONS

'Microconduit' refers to a conduit for conveying or processing fluids which has the smallest cross-section dimension less than 500 μm, preferably less than 200 μm. The minimum cross-section dimension refers to the diameter in the case of circles, the smallest side in rectangles, the minor axis length in ellipses and the smallest distance between opposing faces in polygonal shapes.

'Fluid' refers to a gas or more preferably a polar or non-polar liquid, or combinations thereof.

'Reynolds number' is defined as $\rho Vd/\eta$, where $\rho$ and $\eta$ are the fluid density and viscosity, V is the average velocity averaged over the cross-section of the microconduit, and d is the smallest cross-section dimension of the microconduit.

'Microfluidic device' refers to a device having one or more microconduits for transport and/or processing of fluids.

'Non-deformable' or 'hard' portions refers to portions of the body made of materials having shear elasticity modulus greater than 100 kPa, preferably greater than 500 kPa.

'Deformable' or 'soft' portions refer to portions of the body made of soft materials having shear elasticity modulus less than 100 kPa.

BRIEF DESCRIPTION OF THE DRAWINGS

FIG. 2 (*a*) is a schematic longitudinal cross-sectional view of the microfluidic device of the present invention, depicting a body and a microconduit of the microfluidic device, with non-deformable and deformable sections.

FIG. 2 (*b*) is a schematic vertical cross-sectional view depicting the arrangement of microconduit in the body of the microfluidic device of the present invention, where one of the walls/layers of the microconduit is deformable and the other walls/layers are non-deformable.

FIG. 3 is a schematic plan view of the arrangement of microconduit in the body of the microfluidic device of the present invention, depicting inlets permitting independent fluid streams and an outlet.

FIG. 4(*a*) to FIG. 4(*g*) depict exemplary cross-sectional profiles of the microconduit of the present invention.

FIG. 5 is a schematic longitudinal cross-sectional view of the microfluidic device of the present invention, depicting the body, inlets, outlets that are connected to the microconduit having curved configuration.

FIG. 8 is a schematic longitudinal cross-sectional view of the microfluidic device of the present invention, depicting variable cross-section of the microconduit, along its length.

FIG. 9 (*a*) is a schematic is a schematic longitudinal cross-sectional view of the microfluidic device of the present invention, depicting a body and a microconduit of the microfluidic device, with only a deformable section.

FIG. 9 (*b*) is a schematic vertical cross-sectional view depicting the arrangement of microconduit in the body of the microfluidic device of the present invention, where all the walls/layers of the microconduit is deformable.

FIG. 10 (*a*) is a schematic longitudinal cross-sectional view of the microfluidic device of the present invention, mounted on a base member.

FIG. 10 (*b*) is a schematic vertical cross-sectional view depicting the arrangement of microconduit in the body of the microfluidic device, which is mounted on a base member.

FIG. 11 is a schematic plan view of the microfluidic device of the present invention illustrating a network of micro conduits.

FIG. 12 (*a*) shows a plan view of the microfluidic device comprising the body, inlet and outlet, micro-conduit, hard and soft parts in the presence of flow.

FIG. 12 (*b*) shows a plan view of the microfluidic device comprising the body, inlet and outlet, micro-conduit, hard and soft parts in the presence of flow.

FIG. 12 (*c*) shows an elevation cross-section along the micro-conduit of the microfluidic device comprising the body, inlet and outlet, micro-conduit, hard and soft parts in the presence of flow. Also shown here is the deformation of the deformable part of the microconduit due to the applied pressure gradient, the laminar flow upstream of the deformable portion of the microconduit.

FIG. 12 (*d*) shows a cross-section perpendicular to the micro-conduit of the microfluidic device comprising the body, inlet and outlet, micro-conduit, hard and soft parts in the presence of flow. FIG. 12(*d*) also illustrates the vibration of the deformable section of the microconduit due to the applied pressure gradient, and the disruption of the laminar flow and generation of turbulence in the deformable section.

FIG. 13 is a plan view of an exemplary microfluidic device of the present invention, prepared from a PDMS gel, arranged on a base member, according to the features as shown in FIG. 8.

DETAILED DESCRIPTION OF THE INVENTION

Figure 1:
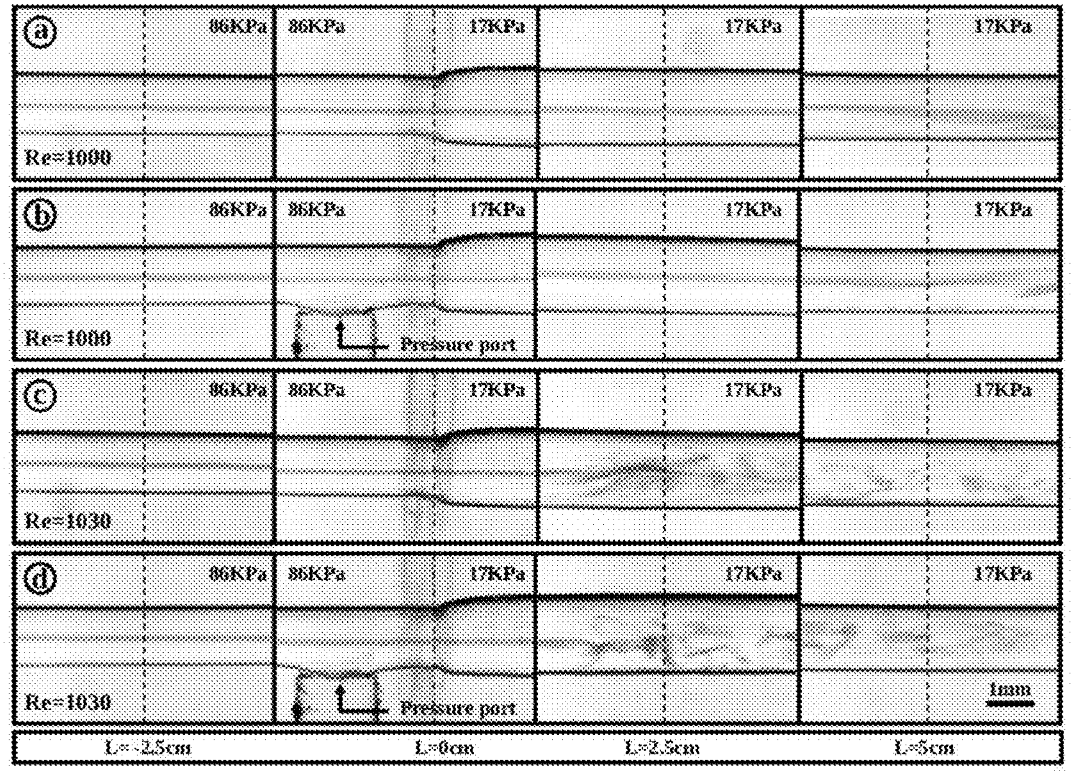
FIG.1 (PRIOR ART)
FIG. 1 an image of the dye stream experiment depicting the extent of mixing of fluids in a known device where a laminar flow of a fluid is disrupted by a soft wall of the device.

Accordingly, the present invention provides a microfluidic device with at least a micro-channel, having a non-deformable section and a deformable section, to trigger instability in the laminar fluid flow, while fluid is transiting through the micro-channel.

In an aspect of the present invention the structure of the microconduit of the microfluidic device is rendered soft enough, so that there is a flow instability, which involves wall oscillations of the microconduit, due to the coupling between the fluid flow and the motion of the walls of the microconduit. This instability occurs at a Reynolds number, which is lower than that for transition through a rigid microconduit of the same dimension, and it generates turbulent flow with significantly enhanced mixing of the selected fluids, in a substantially reduced period of time. For instance, considering the mixing time due to the diffusion of small molecules in a fluid such as water, in a device having a laminar flow of the fluid, having a width of 1 mm, is about 1000 seconds. In comparison, the disruption of the laminar flow of the fluid as induced by the device of the present invention reduces the mixing time to about $10^{-2}$ seconds.

In yet another aspect of the present invention the walls of the microfluidic device or parts of the walls are made of materials which are sufficiently soft (low elasticity modulus) so that the flow of fluid through the conduits is not in the laminar regime, but spontaneously becomes unstable and transitions to a chaotic and highly mixed turbulent state.

In another aspect of the present invention the wall or a portion of the wall, of the micro-conduit is soft enough, so that there is a flow instability, which involves wall vibrations due to the coupling between the fluid and wall motion. This instability occurs at a Reynolds number lower that for transition through a rigid tube or channel, and it generates turbulent flow with significantly enhanced mixing, and a reduction in the mixing time by many orders of magnitude.

In still another aspect of the present invention, the walls of the microconduit are made sufficiently soft in a section of the microconduit, so that a spontaneous instability induced within the fluid which results in mixing. In other words, a spontaneous break-up of the base laminar flow and complete mixing across the microconduit over very short distances of the order of a few centimeters is achieved, while reducing the mixing time to an order of few tens of milliseconds for a microconduit having a height about 100 microns and a width of 1 mm.

In yet another aspect of the present invention, Reynolds number (flow rate) at which the instability is triggered, by modulating the diameter of the conduit and the elastic properties of the wall material of the microconduit. In this way, a control over the flow regime (stable or unstable) is accomplished resulting in the enhanced mixing of the fluid(s). In addition, for a given microconduit having fixed wall properties, the instability is triggered only when the flow rate (Reynolds number) exceeds a critical value. Therefore, the flow regime and the extent of mixing are altered by changing the flow rate.

In further aspect of the present invention, the microfluidic device renders an active mixing without adopting any moving parts. Accordingly, in the device of the present invention no micron-sized moving parts and external actuation are incorporated. In the microfluidic device of the present invention the motion of the walls of the microconduit is spontaneously induced by a dynamical instability of the laminar flow of the fluid. This is advantageous in comparison to passive mixing approaches, since fabrication is very simple and can be done using soft materials; there is no necessity of etching sub-micron scale features or tortuous channels.

In still another aspect of the present invention fluid both polar and non-polar fluids can be used for mixing, since no electrical forces are involved.

In yet another aspect of the present invention the hard materials that are preferably used for the non-deformable portion of the microconduit of the device include polymers, plastics, metals, glass, ceramics and composites.

In still another aspect of the present invention, the deformable materials that are used for the deformable portion of the microconduit are soft elastomeric polymers, which are cross-linked to form gels. In the gelation process, a 'cross-linker' is used to cross-link the polymer chains to form a network which is elastic or flexible. The modulus of elasticity (shear modulus) of the material is varied by changing the cross-link density (number of cross links per unit volume). When the incorporated amount of cross-linker is less, the cross-linking density decreases and thereby decreasing the shear modulus of the deformable materials. In this invention, in an exemplary manner, the preparation of cross-linked polymer gels is performed by soft lithography techniques, and the shear modulus is reduced by decreasing the amount of cross-linking agents during gelation, so that the cross-link density is low.

In further aspect of the present invention, the preferred embodiments pertaining to the dimensions of the microconduit include a height (smallest dimension), in the range of about 20 and 500 microns, a width in the range of 0.2-5 mm, and the length in the range of as 0.5-5 cm.

In yet another aspect of the present invention the viscosity of the fluids that are used for mixing is less than 50 times that of water at an ambient temperature and under atmospheric pressure.

In further aspect of the present invention, the shear modulus of the deformable materials used are less than 100 kPa and more preferably less than 10 kPa.

In still another aspect of the present invention, the maximum flow velocity generated in the microconduit is up to 5 m/s, so that the Reynolds number exceeds the transition Reynolds number for the prescribed micro-channel dimensions, fluid properties and wall shear modulus. The Reynolds number, in the present invention, which is arrived at based on the channel height or tube diameter and average flow velocity, is advantageously less than 500, more preferably less than 200.

In still another aspect of the present invention, the microfluidic device of the present invention generates a turbulent flow with very high cross-stream velocity fluctuations. The velocity fluctuations observed in the invention are at least about 50% of the mean flow velocity, and this generates rapid cross-stream mixing of the fluids. The decrease in the dimensions of the microconduit in the device of the present invention results in a multifold increase in the intensity of the velocity fluctuations and generated true turbulence. This is contrary to conventional wisdom where the intensity of the fluctuations usually decreases as the size of the device decreases.

Due to the large cross-stream velocity fluctuations, the microfluidic device of the present invention generates a very rapid and efficient mixing. In the device of the present invention the mixing index is greater than 0.95 (that is, variation in concentration of less than 5% of the solute across the width of the microconduit) within a microconduit length of 3 cm and the time required for mixing is of tens of milliseconds.

In yet another aspect of the present invention the microconduit is provided with a small minimum cross-section dimension and the smaller length, thereby enabling incorporation of network of microconduits in a single microfluidic device.

In further aspect of the present invention, the disruption of the laminar flow and the chaotic fluid motion in the microfluidic device results in rapid transport of solutes from the fluid to the walls of the microconduit, or vice versa.

In still another aspect of the present invention, the disruption of the laminar flow and the chaotic fluid motion of the fluid results in rapid transport of heat from the fluid to the walls of the microconduit, or vice versa, thereby rapidly increasing/decreasing the temperature of the fluid.

In yet another of the present invention, the disruption of the laminar flow and the chaotic fluid motion results in rapid transport of heat between two or more inlet fluid streams that are initially at different temperatures.

The preferred embodiments of the microfluidic device of the present invention are now described, by initially referring to FIG. 2(*a*) of the accompanied drawings. A microfluidic device 100 of the present invention includes at least a microconduit 106 through which a selected fluid or fluid streams is/are permitted to pass through for enhanced mixing of the fluid(s) having solutes or samples, in a predetermined section of the microconduit. In the present invention, the term "fluid" refers to a gas or preferably polar and non-polar liquid or a combination thereof, which can comprise a soluble sample to be mixed in the fluid. The term "sample" refers to non-limiting examples such as media containing cells, bacteria, viruses, phage, proteins, nucleic acids, serum, blood, organic solvents containing dissolved solutes, oils, dyes, mixtures of organic solvents, chemicals, aqueous solvents and buffers. It is understood here that the term "sample" as used herein includes a fluid containing chemical or biological agents or analytes that can transit through the microfluidic device 100, which require a desirable level of mixing of molecules.

In an aspect of the microfluidic device of the present invention, as illustrated in FIG. 2(*a*), an inlet 101 to permit at least a stream of fluid (not shown in this Figure), with a desired flow rate and a stable laminar flow into a microconduit 106, is connected to a body 103 of the microfluidic device 100. The inlet 101 can be one of a pump, an injector, a micropipette, a reservoir or any such device that can be used to store and inject the selected fluid 102 into the microconduit 106, with a desired flow rate. The desired flow rate in the present invention is in the range of 0-500 ml/minute. The inlet 101 of this device is shown mounted directly on the body 103, in an exemplary manner. The inlet 101 can be the one that is either integrally connected to the body 103 of the microfluidic device 100 or adopted as an external contraption. The inlet 101 as disclosed herein can also be a hole or an aperture formed on the body 103 of the microfluidic device 100, which is advantageously formed by using photoresist techniques or by other suitable means, such as direct engraving onto substrates, chemical etching, punching with a sharp instrument, 3-D printing or soft templating. The inlet 101 can also be provided with sealing arrangements by using materials such as Teflon, for sealing the inlet 101 to the body 103 of the microfluidic device 100. The inlet 101 as shown in FIG. 2 is advantageously arranged perpendicular to surface axis of the body 103 and in fluid communication with the micro conduit 106.

As particularly shown in FIG. 3, in order permit more than one independent streams of fluids, into the microconduit 106, the device of the present invention is provided with two inlets 101*a* and 101*b* that are arranged in Y-shaped configuration to permit two independent streams of fluid into the microconduit 106. In this aspect, two symmetric inlet streams of the fluids, with desired flow rates and stable laminar flow are permitted into the microconduit 106. The two streams of the fluid 102 are merged together at the entrance of the microconduit 106. The flow rates of the fluids in these two inlets 101(*a*) and 101(*b*) are advantageously maintained as equal or can be varied in the ratio of 1:5. The flow rates can also be suitably modified to an extent these do not cause shearing of the walls of the microconduit, particularly, at the interface where the two streams of the liquid 102 meet.

An outlet 107 is connected to the microconduit 106, as particularly shown in FIG. 2(*a*) and FIG. 3. The outlet 107 is used for receiving fluids from the microconduit 106 and transporting it out of the microfluidic device 100. The outlet 107 can be a micropipette, vacuum pump, syringe, reservoir or any other like device, which can collect the mixed fluid 102 from the micro fluidic device 100. The outlet 107 can either be integrally connected to the body 103 of the microfluidic device 100 or adopted as an external contraption. The outlet as disclosed herein can also be in the form of a hole or an aperture formed on the microfluidic device 100, which is advantageously formed by using photoresist techniques or by other suitable means. The outlet can also be provided with a sealing arrangement, such as Teflon for sealing the outlet 107 to the body 103 of the microfluidic device 100.

Now, the preferred embodiments of the body 103 of the microfluidic device 100 are described by referring particularly to FIG. 2(*a*), FIG. 2(*b*) and FIGS. 4(*a*)-(*g*). The body 103 of the microfluidic device 100 acts as a housing or a casing, in which the microconduit 106 is arranged or formed. The configuration of the body 103 can be implemented in different desirable shapes, such as circular, elliptical, rectangular, and polygonal, as shown in FIG. 4(*a*) to FIG. 4(*g*) or a combination of aforementioned configurations. The thickness of the body 103 of the microfluidic device 100 can be suitably varied in the preferred range of 100 μm to 1 cm. The body 103 is arranged to be in fluid communication with the inlets as particularly shown in FIG. 2(*a*) and FIG. 3. It is also within the purview of the invention to adopt a multi-walled or a multi-layered structure for the body 103. The walled-structure of the body 103 is advantageously formed from materials having variable elasticity modulus thereby rendering a structure having a combination of hard and soft layers (visco-elastic layers). The advantage of having variable elasticity is that the shape of the microconduit 106 can be altered in such a way that the flow profile is varied and this variation in the flow profile is used increase or decrease the flow rate of the fluid 102 at which there is a disruption of the laminar flow. The stress factor of the visco-elastic layers respond and change in accordance with applied strain, while the fluid 102 is transiting through the microconduit 106. The body 103 is advantageously formed as solid structure and adapted to react to the applied strain. The material for the body 103 can be made of glass, metal, ceramics, composites, plastics, rubbers, or more preferably polymeric compounds that can be cross-linked to form gels, such as polydimethylsiloxane (PDMS), polyacrylamide, polyvinyl chloride, styrene-butadiene polymers, silicones, polymethyl methacrylates, polycarbonates, and other such polymers. In the present invention PDMS is used as a preferred material.

In the microfluidic device 100 of the present invention the body 103 is provided with an integrated combination of a non-deformable portion 104 and a deformable portion 105, which are in fluid communication with each other, as particularly shown in FIG. 2(*a*).

The non-deformable portion 104 of the body 103 is arranged in fluid communication with the inlet 101, as shown in FIG. 2(*a*). The non-deformable portion 104 is made of glass, metal, ceramic, plastic, rubber or a combination thereof. Preferably, polymeric compounds that can be cross-linked to form gels, such as polydimethylsiloxane (PDMS), polyacrylamide, polyvinyl chloride, styrene-butadiene polymers, silicones, polymethyl methacrylates, polycarbonates and other such polymers, are advantageously used for preparing the non-deformable portion 104. The non-deformable portion 104 may be made as a single integral unit or multiple units that can be bonded or fastened together. The non-deformable portion 104 is advantageously arranged in close proximity to the inlet 101. The non-deformable portion 104 may also be made by selectively hardening the parts of a deformable portion 105, by adding catalyst or cross-linker to increase the cross-link density or by other means, such as solvent evaporation or drying or curing to harden a substance, or bond breaking by heat, chemicals or ultraviolet radiation. The material for the non-deformable portion 104 of the microconduit 106 is adopted to possess a shear elasticity modulus greater than 100 kPa, preferably greater than 500 kPa, so that the shape and integrity of the microfluidic device 100 is maintained and the microfluidic device does not deform significantly under the applied pressure gradient.

The deformable portion 105, which is integrally connected to the non-deformable portion 104, is made of soft materials that are cross-linked to form gels, such as polydimethylsiloxane (PDMS), polyacrylamide, polyvinyl chloride, styrene-butadiene polymers, silicones, polymethyl methacrylates, polycarbonates and other such polymers. The deformable portion 105 is adopted in such a way that the cross-link density in the deformable portion 105 is low, and the shear modulus of the deformable portion 105 is less than 100 kPa. This is implemented by reducing the concentration of the cross-linker, while cross-linking the polymer. In this invention the preferred cross-linkers that used are sulphur in rubber, methylenebisacrylamide for polyacrylamide gel, siloxane cross-linkers for polydimethylsiloxane gels. Alternately, the elasticity modulus is varied by incorporating a catalyst, which is used for initiating the cross-linking reaction. The catalyst is selected from platinum-based catalysts for polydimethylsiloxane or tetramethylene diamine (TEMED) for polyacrylamide gels, free radical vinyl polymerisation for polycarbonate, cross-linking by gamma radiation or sulphur for styrene butadiene polymers. The deformable portion 105 can also be made with soft rubbers or elastomeric materials having a sufficiently low shear modulus, or by soft biological materials.

The non-deformable portion 104 and the deformable portion 105 are contiguously arranged to each other to create an environment where a substantially laminar flow of the fluid spontaneously meets with its spontaneous disruption in the deformable portion 105. It is advantageous to have a non-deformable portion 104, arranged in close proximity to the inlet 101 so as prevent any possible leakage at the joints.

As shown in FIG. 2(*a*) and FIG. 2(*b*), the microconduit 106 is formed as a hollow conduit that is in the non-deformable portion 104 and the deformable portion 105 of the body 103 and is in flow communication with the inlet 101 to receive the fluid. In other words, the surfaces of the non-deformable portion 104 and the deformable portion 105 form an external casing or walls for the microconduit 106. The deformable portion 105 of the microconduit facilitates a dynamic interaction between the fluid and the deformable portion 105. In other words, the microconduit 106 is integrally contoured to form a hollow and longitudinal conduit that passes through the body 103, as shown in FIG. 2(*a*) and FIG. 2(*b*). Therefore, the microconduit 106, of the present invention, demonstrates a structure having variable elastic modulus i.e., having a combination of hard (non-deformable) and soft (deformable) portions.

As shown in FIG. 2(*b*), the microconduit 106 thus formed is abutted by three walls of non-deformable of portion of the body 103 and by one wall of deformable portion of the body 103.

The configuration of the microconduit 106 can be implemented in different desirable shapes 106 such as circular, elliptical, rectangular, polygonal or any combination thereof, as shown in FIG. 4 (*a*) to (*g*).

The microfluidic device 100 of the present invention is provided with a microconduit 106 of reduced length, which is in the range of 1-5 cm, preferably in the range of 1-3 cm. The small length of the microconduit is necessary for constructing microfluidic devices which occupy small area, require small volumes of samples and reagents, and requires small pressures for driving the flow. The microfluidic device 100 of the present invention facilitates an enhanced mixing of the fluid(s) using high velocity, and small microconduit lengths. Moreover, deformable portion of the microconduit 100 also significantly reduces the pressure required for driving the flow, since the microconduit 100 can expand and reduce the resistance to the flow. In order to achieve large flow rates with small pressure differences of about 0.5 atm or less for a microconduit of width 1.5 mm and height less than 100-200 μm, the microconduit 100 length less than 5 cm, preferably less than 3 cm is provided.

The microconduit 106 as shown in FIG. 2(*a*), is exemplarily shown as having a straight hollow structure, of uniform internal diameter, extending longitudinally through the body 103, from the inlet 101 and connected to the outlet 107, by forming a microfluidic tunnel between the inlet 101 and the outlet 107 covered by the walls of non-deformable 104 and deformable 105 portions of the body 103. The microconduit 106 of the present invention can also be implemented with other profiles such as a curved profiled as shown in FIG. 5, where the microconduit 106 is connected to the inlets 101(*a*) and 101(*b*) and outlet 107. It is within the purview of the invention to adopt other suitable geometrical shapes such as helical, for implementing the flow and mixing of the fluids.

Figure 6:
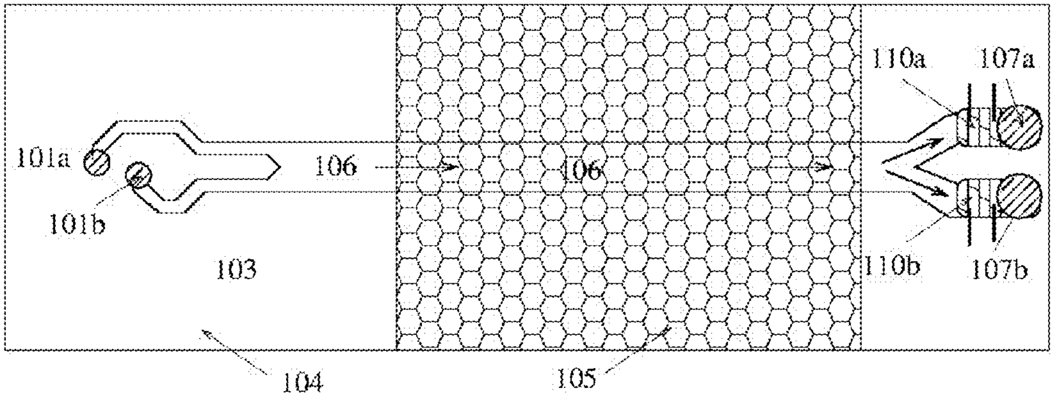
FIG. 6 is a schematic plan view, of the microfluidic device of the present invention, illustrating the connectivity of impendence measurement arrangement.

As shown in FIG. 6, an arrangement of independent inlets 101*a* and 101*b* are connected to a combination of non-deformable 104 and deformable portions 105 of the body 103, along with devices for qualitative and quantitative analysis of the samples, such as impedance measurement devices 110*a* and 110*b*, which are connected to the outlets 107*a* and 107*b*. The on-line impedance measurement is used for measuring the conductivity of the two fluids passing between electrodes immersed in the fluid on the sides of the walls or in a reservoir at the outlet. It could also be used for other purposes such as counting and sorting cells if an alternating voltage is applied across the electrodes, or for applying an electric field for purposes such as sorting cells. Such an arrangement also enables different types of devices to be mounted at the outlet and different kinds of measurements to be conducted on the samples such as fluorescence measurements, imaging and image analysis, spectroscopy etc. Thus, the rapid mixing generated by the device of the present invention, significantly enhances the range of measurements and manipulation that is possible in microfluidic devices.

Figure 7:
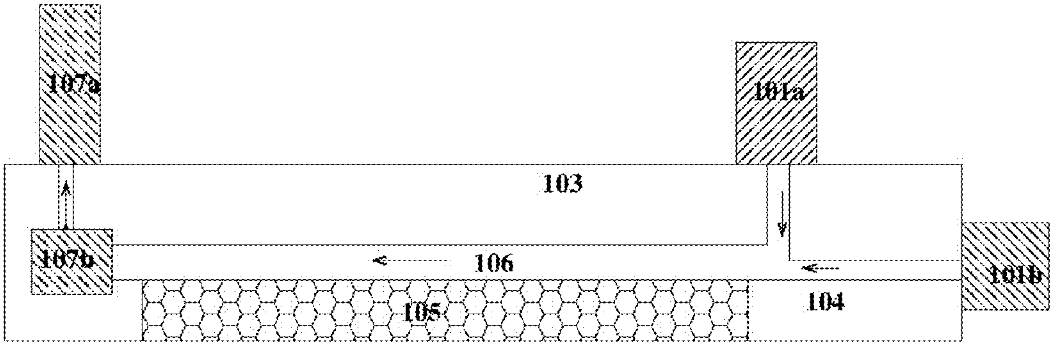
FIG. 7 is schematic cross-sectional view of the microfluidic device of the present invention showing vertical and horizontal arrangement of inlets and outlets.

In an aspect as shown in FIG. 7, the inlet 101*a* is arranged substantially vertical to the longitudinal axis of the microconduit 106 and whereas the inlet 101*b* is arranged along the longitudinal axis of the microconduit 106, to facilitate the inflow of two streams of the selected fluid, from two planes or directions. The corresponding outlet 107*a* is arranged substantially vertical to the longitudinal axis of the microconduit 106 and the outlet 107*b* is arranged along the longitudinal axis of the microconduit 106. It is understood here that the total number of inlets can be suitably varied depending on the requirement of number of fluid streams and these inlets can also be arranged at various other convenient locations of the body 103 of the microfluidic device 100. The location of the inlets often depends on the ease of fabrication and the facility for interconnecting with the external inputs and outputs. In micro-tubes, it is more convenient to have inlets and outlets aligned with the axis of the tube, in order to reduce flow resistance. In micro-channels, holes are often punched on one of the layers which are bonded to construct the micro-channel. In this case, it is convenient to have inlets and outlets perpendicular to the direction of the microconduit. In some cases, external constraints may require inlets and outlets above, below and on the sides of the body. In other words, the microfluidic device 100 of the present invention can be configured to support a multi-directional flow of fluids into the micro conduit 106.

In still another aspect of the present invention as shown in FIG. 8, the microconduit 106 is provided with a configuration of varying internal diameter along its length. The variation in the dimension of the microconduit 106 results in a modification in the flow profile of the fluid, resulting in the reduction or increase in the flow rate (Reynolds number), at which the laminar flow of the fluid is spontaneously disrupted. The dimensions of the microconduit 106 can also be suitable configured to facilitate a controlled deformation, upon the application of a pressure difference between the two ends, so as to reduce or increase the flow rate (Reynolds number) of the fluid, at which there is a disruption in the laminar flow of the fluid.

The microconduit 106 is provided with a profile having a diameter in the range of 20-500 μm for microconduits with circular cross sections, smallest side in the range of 20-500 μm for microconduits of rectangular cross section, minor axis in the range of 20-500 μm for microconduits of elliptical cross section, and smallest distance between opposite sides in the range of about 20 μm to 500 μm for microconduits with polygonal cross section.

In yet another exemplary aspect of the present invention, as shown in FIG. 9(*a*) and FIG. 9(*b*), the body 103 is provided with a microconduit 106, which is formed only with a deformable portion 105, to provide an enhanced work area for the mixing of fluid in the micro conduit 106.

In yet another exemplary aspect of this invention, the said body 103 of the device is disposed on a based member 108, as shown in FIG. 10. The material for the based member 108 is one of glass, polymer, plastic, metal, composite, ceramic or a combination thereof. The base member 108 is preferred for mounting the device, for structural stability and support for the device, for mounting inlets, outlets or appendages for measurements, and for positioning the device relative to other equipment.

In another aspect of this invention, as shown in FIG. 11, a network of interconnected multiple microconduits 106*a*, 106*b* and 106*c*, is formed in the body 103 of the microfluidic device 100, having a combination of non-deformable 104 and deformable portions 105, to function as a single coordinated unit. The microfluidic device is provided with a combination of inlets and outlets 101*a*, 101*b*, 101*c*, 101*d*, 107*a*, 101*e*, 101*f*, 107*b*, 107*c* and 101*g*. In this arrangement, the outlet for one microconduit can serve as the inlet for another microconduit, or the inlets and outlets could be connected to external reservoirs. In one embodiment of this invention, the reservoirs containing the inlet and outlet fluids are mounted on the device and the device is fluidically insulated from the surroundings, apart from the sample inlet and the waste outlet. This embodiment has several important advantages, including the insulation of the samples and reagents from the outside thus preventing contamination, and reducing the dead volume, the volume of reagents, samples and waste. In another embodiment, the inlets and outlets are connected to external devices which are fluidically connected to the surroundings. 109*b* and 109*c* are used. The valves can be either active or passive. Passive valves permit flow only in one direction, and prevent back flow. Passive valves, which permit flow only in one direction, are prepared using flexible converging channels, wherein the flow in the direction of convergence is facilitated by the expansion of the channel, while the flow in the opposite direction is prevented since the pressure gradient causes the channel to close. Active valves are disposed to be driven by a variety of means, including pressure, electrical or magnetic actuation, or other suitable means. Valves can also be mounted on the same body of the device to control the flow as necessary. The flow in microconduits is also regulated by a pneumatic method, involving the perpendicular arrangement of a control microconduit above or below another microconduit. When the control microconduit is pressurized, it pinches off the control microconduit and cuts off the flow of the fluid. By regulating the pressure in control microconduit, it is possible to regulate the flow rate in other microconduits. Another method for controlling the flow of the fluid is to use magnetic coils coupled with a magneto-rheological fluid, where the magnetization of the fluid results in an expansion, which can cut off flow in the microconduit. Other simpler methods include, mechanical pinching off from outside, or by bending or folding the entire assembly. Electrical actuation another method, where an electric field can be used to deform the walls of the microconduit and control the flow. An impedance measuring device 110 is also connected to network of microconduits to measure impedance.

The functional aspects of the micro fluidic device of the present invention are now described by particularly referring to FIG. 12(*a*) to FIG. 12(*d*). The microconduit device 106 as shown in FIG. 12(*a*), is connected to the inlet 101 to permit the fluid, in a substantial laminar flow 102*a* conditions, at a pre-determined flow rate, into the microconduit 106. The substantial laminar flow of the fluid 102*a* is maintained in the non-deformable portion of the body 103 or the microconduit 106. As the fluid transits through the microconduit 106, the flow rate of the fluid experiences a spontaneous disruption once it enters into the deformable portion 105 accompanied with the vibration of the deformable portion 105, whenever the fluid flow rate crosses a threshold value. In this context, the threshold value of the fluid flow rate corresponds to a Reynolds Number (Re), which is less than the transition Reynolds Number for a rigid or hard microconduit of the same dimensions. It is relevant to note here that the transition Reynolds number in rigid conduits depends also on the shape of the conduit. For instance, the transition Reynolds number for the flow in a rigid tube is 2100, whereas that for the flow in a channel of infinite width is about 1000. In the present microfluidic device of the present invention the Reynolds number for transition is reduced significantly below that for a rigid microconduit of the same dimensions with the incorporation of the deformable portion. The vibration of the wall of the microconduit 106 is shown in FIG. 12(*b*). The laminar flow of the fluid 102*a* in the non-deformable portion 104 experiences a sudden trough in the deformable portion 105 as shown in FIG. 12(*c*); thereby the flow rate crosses the threshold value causing the disruption in the laminar flow of the fluid as shown in FIG. 12(*d*). Consequently, the disruption in the laminar flow of the fluid induces a spontaneous turbulence in the fluid, facilitating an enhanced mixing of the fluid, fluid with solutes or different streams of fluids, in a lesser period of time.

Figure 14A:
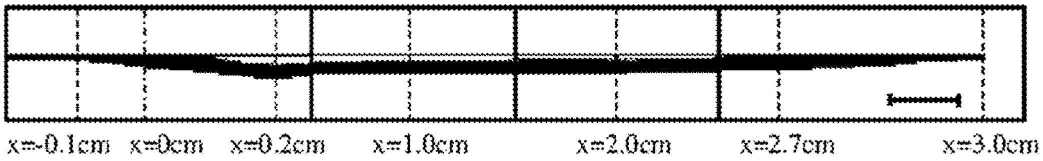
FIGS. 14 (*a*) and 14(*b*) depict an exemplary elevation cross section (A) and the cross section perpendicular to flow (B) of fluid, at different downstream locations of the microconduit under pressure gradient.
Figure 14B:
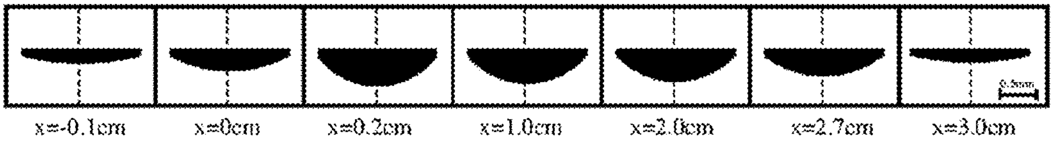

In yet another aspect of the present invention an exemplary microfluidic device of the present invention is as shown in FIG. 13 having with two layers, where the top layer is made of hard polydimethylsiloxane (PDMS) gel with a shear modulus about 0.55 mPa, in which an indentation in the form of the pattern shown in FIG. 6 is transferred from an pattern made on silicon using a polymer such as SU8 photoresist. In this exemplary embodiment, the width and height of the indentation are about 1.5 mm and 100 m respectively, and the length of the straight portion of the channel is about 3 cm. The bottom surface is made of PDMS in which the cross-linker (catalyst) concentration has been decreased in order to achieve a shear modulus in the range 17-54 kPa. The bottom surface is mounted onto a glass base. The top surface is bonded onto the bottom surface using a small amount of cross-linker, to provide a microconduit 106 of width 1.5 mm, height about 100 m and length about 3 cm. Inlet holes are punched in the top surface of the body, and micropipette tips are fitted into the inlet holes in such a way that there is no leakage. The micropipette tips are connected to individual syringe pumps using tubes, and the selected fluid is pumped into the inlets at controlled flow rates using the syringe pumps. The fluid is collected from separate outlets in order to examine the extent of mixing in the flow. The outlets are also punched into the top PDMS layer, and micropipette tips are fitted into the holes in such a way that there are no leaks. The fluid streams are analyzed using impedance measurements separately in two micro surge tanks mounted on the body, and then the fluid streams leave from the outlets. The downstream flow of the fluid in the deformed microconduit is shown in FIG. 14(*a*) and the cross section perpendicular to flow at different downstream locations is shown in FIG. 14(*b*), where the indicated values of "x" refers to the length of the microconduit in centimeters, and x=0 is at the joint between the non-deformable and deformable sections of the bottom wall. The figure shows the deformed shape of the channel when a pressure difference is applied to generate fluid flow. The length of the non-deformable portion of the microconduit 100 is exemplarily shown as 0.8 cm, the length of the deformable portion is 3 cm, the width is 1.5 mm and the height is 100 m.

The microconduit 106 is exemplarily formed as a single unit, by forming a cast in the form of the outer body, and a template in the form of a thin object such as a glass rod of the desired shape is suitably placed in the cast. The gelation mixture made from the aforementioned material is poured into the cast and cross-linked. The template is then carefully removed to construct a hollow bore or tunnel within the block of the body. Alternately, the microconduit 106 can also be formed as a hollow space created between two or more layers. A pattern could be transferred onto one of the layers of the microconduit 106 using soft lithography, engraving or some other means, and the other layer could be bonded onto the first to form the microconduit of the desired shape and cross section.

Figure 15:
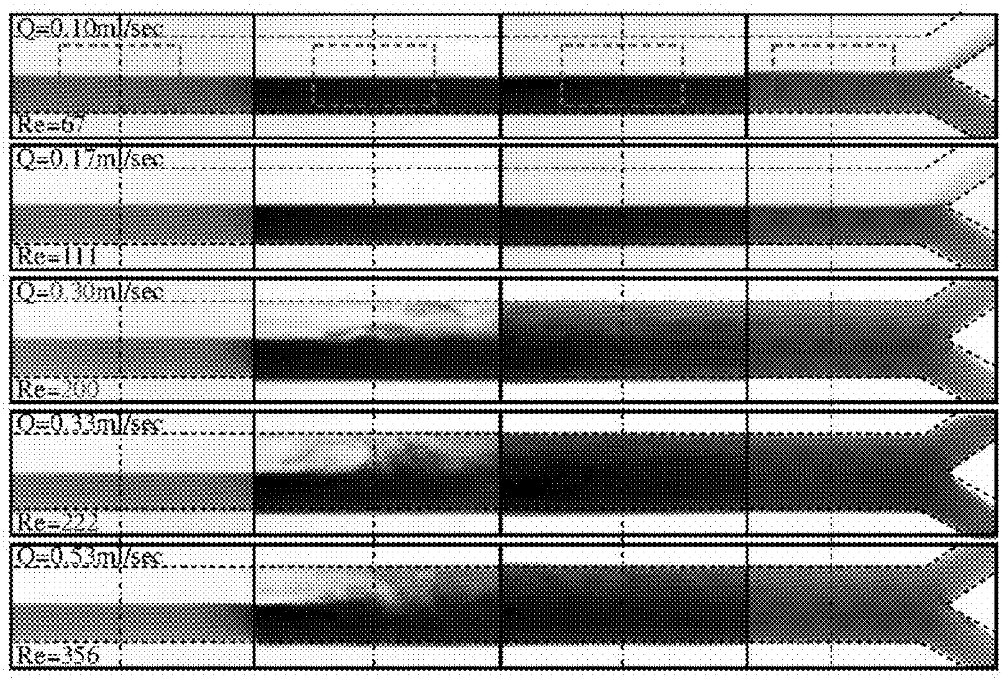
FIG. 15 illustrates a mixing of streams of clear fluid and a dye stream while transiting through the microconduit of the present invention in which clear fluid is pumped through one inlet and black dye through the other inlet, at different Reynolds number in the microfluidic device displayed in FIG. 13.

In order to examine the extent of mixing of the fluids within the microconduit, a dye is injected into one inlet and clear fluid is injected into the other inlet. The images as shown in FIG. 15 along the length of the microconduit reveal the extent to which there is mixing between the two streams. The images reveal that at low flow rates, there is no mixing between the two streams. However, when the flow rate or Reynolds number crosses a threshold value, there is a disruption of the laminar flow and rapid mixing between the two streams, which establishes the dependence of the transition Reynolds number on the shear modulus of the soft wall of the microconduit. In this exemplary embodiment, the flow velocities at transition under study are 1-10 m/s, while the length of the microconduit is 3 cm. Therefore, the travel time for the fluid in the microconduit is few tens of milliseconds or less. As can be seen in FIG. 15, the complete mixing of the fluid is achieved within a few tens of milliseconds, thus establishing the fact that the microfluidic device of the present invention can be used for rapid mixing in a reduced period of time. The threshold Reynolds number for transition for this flow is found to depend on the shear elasticity modulus of the deformable surface. The Reynolds number decreases from about 330 when the soft surface has a shear modulus of 54 kPa, to about 200 when the soft surface has a shear modulus of 17 kPa.

The average flow velocity in the microconduit is of the order or 1-5 m/s at transition, while the length of the microconduit is 3 cm. Accordingly, in the microconduit 106 of the present invention the reduced time period of time for the mixing of the fluid is less than 0.1 s.

Figure 16:
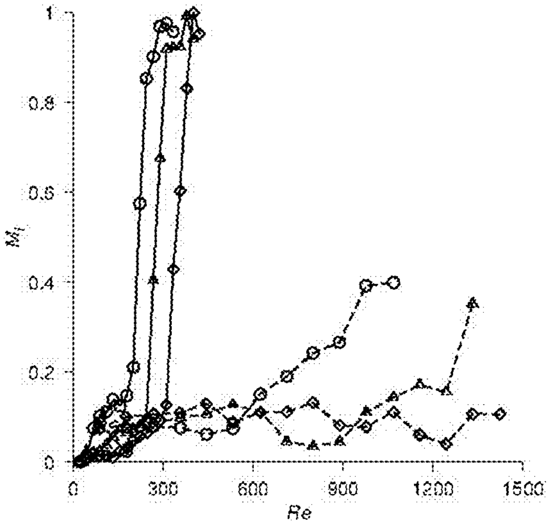
FIG. 16 demonstrates mixing index as a function of Reynolds number at the outlet of the microconduit of the present invention, as well as in prior disclosed work on deformable tubes of diameter 1.2 mm and length 10 cm.

The mixing index for the mixing at the outlet the present invention in a channel of width 1.5 mm, height 100 μm and length 3 cm is shown as a function of Reynolds number by the solid lines in FIG. 16 for deformable portions made with different shear elasticity moduli. It is evident from the figure that the mixing index is very low in the laminar flow, increases dramatically at transition and close to 1 in the turbulent flow. Whereas, the mixing index in the known devices for the flow in a soft tube of diameter 1.2 mm and length 10 cm is shown in by the dashed lines in FIG. 16. It is clear that in a known device, the desired level of mixing is not achieved even after a flow length of 10 cm. Per contra, in the microfluidic device 100 of the present invention, perfect mixing is achieved in a microconduit length of less than 3 cm, at very low Reynolds number.

Figure 17:
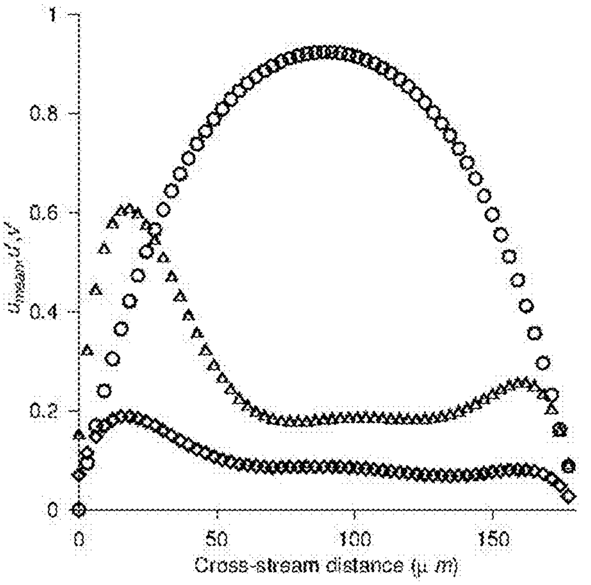
FIG. 17 depicts the mean velocity (circle), root mean square of the velocity fluctuations in the flow direction (triangle) and root mean square of the velocity fluctuations in the cross-stream direction (diamond) as a function of the cross-stream distance from the soft surface for a microconduit of length 3 cm, width 1.5 mm and height 100 μm shown in FIG. 13 at a Reynolds number of 250.

The dramatic increase in mixing index is due to the large turbulent velocity fluctuations generated by the microfluidic device 100 of the present invention. Direct measurements of the mean velocity and the velocity fluctuations by Particle Image Velocimetry across an exemplary microconduit of length 3 cm, width 1.5 mm and height 180 m are shown in FIG. 17, where the mean velocity is shown by triangles, the root mean square of the velocity fluctuations in the flow direction is shown by triangles and the root mean square of the velocity fluctuations in the cross-stream direction is shown by the diamonds. It is clearly observed that the root mean square of the velocity fluctuations is up to 50% of the mean velocity, indicating very high turbulence intensity in a small microconduit. The turbulent velocity fluctuations in the microfluidic device 100 of the present invention is also much higher than the intensities of about 10% observed in the aforementioned prior study on the flow through a flexible tube of diameter 1.2 and 0.8 mm. This is contrary to the expectation from conventional wisdom that the turbulent velocity fluctuations should decrease as the size of the conduit decreases.

Figure 18:
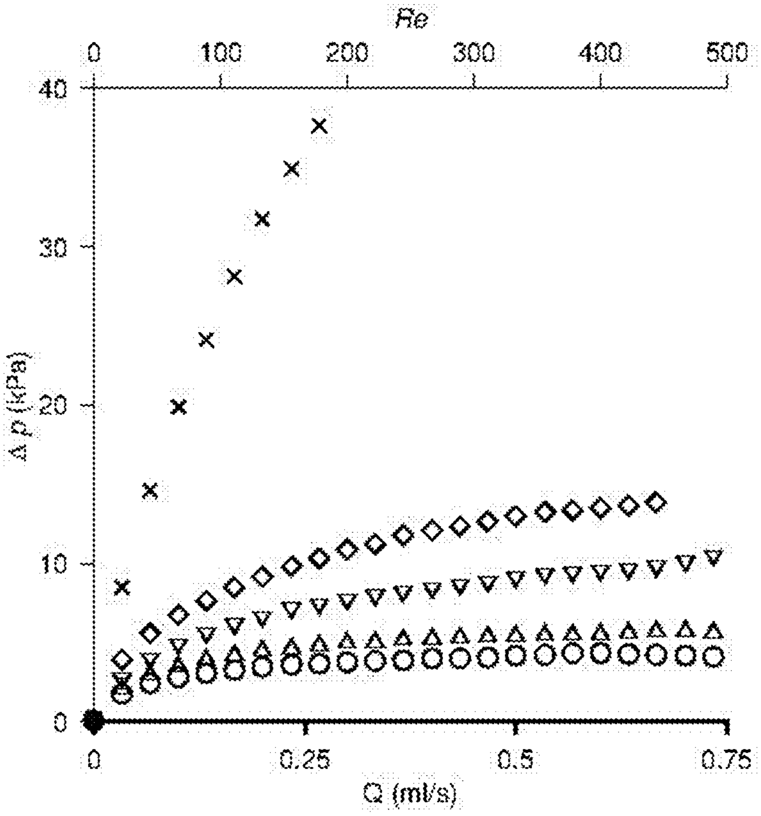
FIG. 18 shows the pressure difference required to drive the flow as a function of the flow rate and Reynolds number for the microfluidic device shown in FIG. 13 when the deformable portion is made with shear modulus 18 kPa (circle), 24 kPa (triangle with upward vertex), 38 kPa (triangle with downward vertex), 54 kPa (diamond) and 550 kPa (cross).

This turbulence and rapid mixing is achieved at very low pressure difference or energy cost. The pressure difference is reduced due to the deformability of the deformable material used, and the consequent expansion when the flow is generated. The pressure difference is less than 0.5 atm or less, and increases very little when the flow rate is increased. As shown in FIG. 18, the pressure difference is smaller by a factor of at least 10 for a deformable portion with shear modulus less than 54 kPa, in comparison to that for a non-deformable portion is made with shear modulus 550 kPa.

In diagnostic applications and for analyzing the chemical and biological compositions of the reactants and production, it is may become necessary to have additional devices for qualitative and quantitative analysis, such as impedance measurements, fluorescence measurements, imaging and image analysis, spectroscopy etc., of the fluid transiting through the microfluidic device could be integrated into the same body. These features can also be integrated onto the body of the microfluidic device.

Various modifications to the present invention will become apparent to those skilled in the art from the foregoing description and accompanying drawings. Accordingly, the present invention is to be limited solely by the scope of the following claims.

We claim:

1. A microfluidic device, comprising:

at least an inlet to permit at least a stream of fluid with a desired fluid flow rate and a stable laminar flow;

a body with at least a non-deformable portion and a deformable portion, with a desired shear moduli, is in fluid communication with said inlet and disposed to receive said fluid;

at least a microconduit of substantially reduced length in the range of 1-5 cm, and cross-section having a diameter in the range of about 20-500 μm, integrally formed in said non-deformable and deformable portions, and is in fluid communication with said inlet;

said deformable portion disposed to spontaneously disrupt stable laminar flow of said fluid, with a vibration, when said fluid flow rate crosses a threshold value and to effect an enhanced mixing, in a reduced period of time with a reduced pressure difference; and at least an outlet disposed to collect said mixed fluid from said deformable portion.

2. The device as claimed in claim 1, wherein said at least two inlets and two outlets, in fluid communication with said microconduit, said inlets and disposed to permit streams of fluids.

3. The device as claimed in claim 1, wherein said flow rate is in the range of 0-500 ml/min.

4. The device as claimed in claim 1, wherein the material for said body is glass, metal, ceramics, composites, plastics, rubbers, gels formed from the cross-linked polymeric compounds selected from the group consisting of polydimethylsiloxane (PDMS), polyacrylamide, polyvinyl chloride, styrene-butadiene polymers, silicones, polymethyl methacrylates, polycarbonates, preferably PDMS.

5. The device as claimed in claim 1, wherein the shear elasticity modulus of said nondeformable portion is greater than 100 kPa, preferably greater than 500 kPa.

6. The device as claimed in claim 1, wherein the shear elasticity modulus of said deformable portion is 100 kPa or less.

7. The device as claimed in claim 1, wherein said body includes only a deformable portion.

8. The device as claimed in claim 1, wherein the cross-sectional profile of said body and said microconduit is one of circular, elliptical, rectangular, polygonal or a combination thereof.

9. The device as claimed in claim 1, wherein the reduced length of the microconduit, preferably in the range of 1-3 cm.

10. The device as claimed in claim 1, wherein the longitudinal profile of said microconduit is curved.

11. The device as claimed in claim 1, wherein the cross-sectional profile of said microconduit is uniform or variable, along its length.

12. The device as claimed in claim 1, wherein said fluid is disposed in said deformable portion for mixing for a period less than 0.1 s.

13. The device as claimed in claim 1, wherein the reduced pressure difference is about 0.5 atm or less.

14. The device as claimed in claim 1, wherein said body is disposed on a base member.

15. The device as claimed in claim 13, wherein the material for the base member is one of glass, polymer, plastic, metal or a combination thereof.

16. The device as claimed in claim 1, wherein said threshold value of said fluid flow rate corresponds to a Reynolds Number (Re), which is less than the transition Reynolds Number for a rigid conduit of the same dimensions.

17. The device claimed in claim 1, wherein said inlet and outlet disposed on top, bottom or side portions of said body.

18. The device as claimed in claim 1, wherein a network of said microconduits, integrally formed in said non-deformable and deformable portions of said body and disposed in fluid communication with inlets, outlets and valves.

* * * * *